United States Patent [19]

Daniel

[11] 4,276,491
[45] Jun. 30, 1981

[54] FOCUSING PIEZOELECTRIC ULTRASONIC MEDICAL DIAGNOSTIC SYSTEM

[75] Inventor: Keith P. Daniel, Gordon, Australia

[73] Assignee: Ausonics Pty. Limited, Lane Cov., Australia

[21] Appl. No.: 81,272

[22] Filed: Oct. 2, 1979

[51] Int. Cl.³ ............................................. H01L 41/08
[52] U.S. Cl. .................................. 310/317; 310/334; 310/335; 310/371; 128/660
[58] Field of Search ................................ 310/334–337, 310/371, 367, 366, 317; 128/660

[56] References Cited

U.S. PATENT DOCUMENTS

| | | | |
|---|---|---|---|
| 2,645,727 | 7/1953 | Willard | 310/371 X |
| 3,292,018 | 12/1966 | Clynes | 310/334 |
| 3,355,603 | 11/1967 | Hesse et al. | 310/366 |
| 4,096,756 | 6/1978 | Alphonse | 310/334 X |
| 4,181,864 | 1/1980 | Etzold | 310/366 X |

Primary Examiner—Mark O. Budd
Attorney, Agent, or Firm—Gottlieb, Rackman & Reisman

[57] ABSTRACT

There is disclosed an ultrasonic piezoelectric transducer consisting of two separate transducer elements bonded together. The individual elements may be similar or different in size, thickness, and/or material. The material which bonds the two elements together may serve as one electrode, and two other electrodes coat the outer surfaces of the two individual elements. By switching the electrodes which are connected to the transmit and receive circuits of an ultrasonic medical scanning apparatus, the single transducer may be used for imaging with high resolution at one frequency, and for pulse Doppler velocity measurements at a different frequency. The two elements may be driven individually or in combination, in order to achieve different operating frequencies and focusings.

5 Claims, 9 Drawing Figures

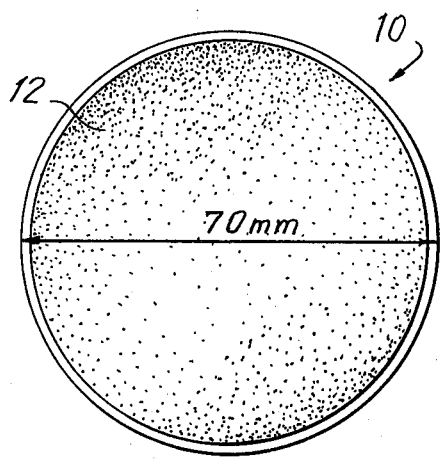
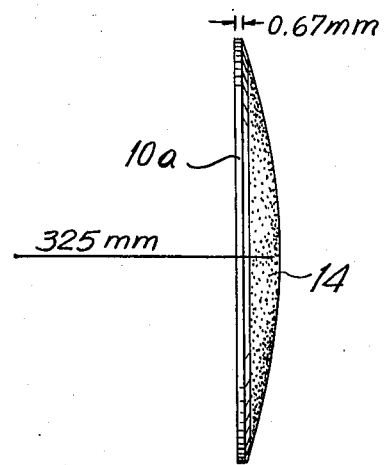
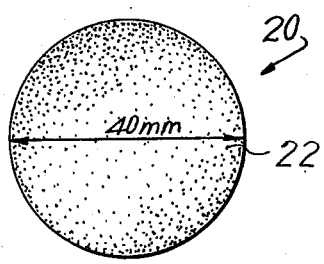
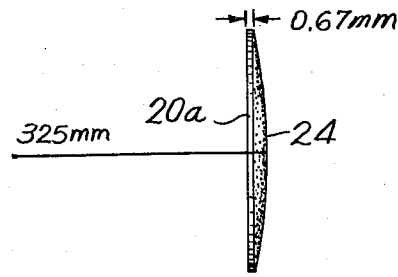
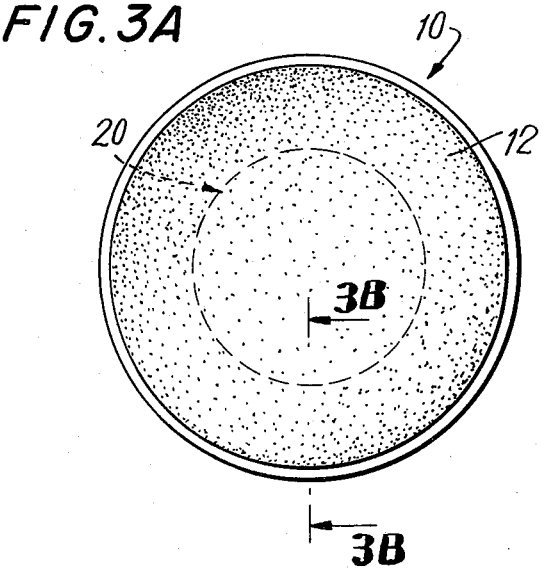
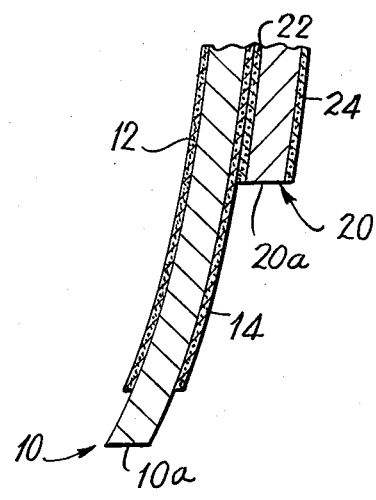

FOCUSING PIEZOELECTRIC ULTRASONIC MEDICAL DIAGNOSTIC SYSTEM

This invention relates to ultrasonic transducers, and more particularly (but not exclusively) to ultrasonic transducers for use in medical diagnostic equipments.

Ultrasounds, or ultra high-frequency sound waves, are being used more and more routinely to examine the interior of a body painlessly, and with a minimum of risk and expense. The conventional pulse echo technique, based on the similar technique used in sonar systems, involves emitting a short pulse of ultrasonic energy, typically in the 1–30 MHz frequency range, into a patient. Any acoustic impedance discontinuity reflects some of the energy in the form of an echo. The time taken for the echo to be returned following transmission of the pulse is a measure of the distance of the discontinuity from the pulse source. In human body tissues, the velocity of sound is more or less constant, ranging from 1450 meters per second in fat to 1600 meters per second in muscle. Although the difference between the impedances of different tissues is small, and the echoes reflected by the boundaries between them are therefore faint, they are large enough to be detected by sensitive receivers. Ultrasonic "echography" has proved to be of particular value as a diagnostic aid in the abdomen and pregnant uterus, eye, breast, brain, lung, kidney, liver and heart. These and other areas of soft tissue include little bone and air, and are therefore suitable for ultrasound examination.

The present invention is not limited to medical diagnostic equipments, and it certainly is not limited to the particular imaging systems which are to be found in the medical field. Nevertheless, in order to appreciate the problem toward which the invention is directed, it will be helpful to consider the different types of ultrasonic systems which are used in present-day medical diagnostic equipments.

As described above, pulse-echo information can be used to determine the distance of a discontinuity from the sounc source. In a conventional A-scan display, a horizontal sweep across a cathode ray tube is triggered by the transmission of an ultrasound pulse. Each echo results in a vertical deflection whose amplitude is proportional to the strength of the echo. Thus the relative positions of the pulses along the X axis of the A-scan display represent the relative positions of organ interfaces in the body, and the relative amplitudes of the pulses represent the types of discontinuities which originated the echoes. "A Mode" displays are particularly useful to measure the size of a baby's head inside the uterus, the depth of the eye and the bladder, and to locate the mid-line of the brain. A B-scan display is similar except that instead of controlling vertical deflections, it is the intensity of the electron beam which is modulated by the strengths of the returning echoes. As is known in the art, such a system may utilize moving recording paper; as the bright dots on the display move back and forth within small ranges, the resulting traces represent the movements of different organ boundaries as a function of time (measured along the length of the paper)—an M-type display. Such a display is particularly useful to demonstrate the pulsatile movements of various parts of the heart and the brain.

More recently, two-dimensional scanners have been developed. In such scanners, an ultrasonic probe is mounted on a mechanical arm that is moved in two dimensions. B-scan type information is developed for numerous positions of the probe and directions of the ultrasonic beam. The term "B scan" has come to be associated primarily with this embodiment. By processing all of the data (echo time and amplitude information), a two-dimensional display may be formed which provides an image of a cross-sectional slice through the body.

In some two-dimensional scanning systems of this type, the probe is held in direct contact with the skin, but skilled operators are usually required for such procedures. In order to automate the procedure, two-dimensional scanners have been developed in which the transducer moves on an arm in a bath of water. The ultrasound is coupled into the patient either by immersing the patient in the water, or by placing the patient on a flexible membrane that forms one of the walls of the bath. Especially in systems of this type, it is not feasible to replace one transducer at the end of the arm by another. Yet for reasons which will become apparent below, it is often necessary to change an operating frequency, depth of focus, etc., and in the prior art this has required a change of transducer.

Doppler scanning systems also rely on echoes, but involve a different operating principle. If an ultrasound wave is reflected from a target that has a component of motion along the direction of the transmitted beam, the reflected wave has its frequency shifted by the Doppler effect. Movement of the target toward the probe causes an increase in frequency, and movement of the target away from the probe causes a decrease in frequency. The frequency shift is proportional both to the frequency of the transmitted beam and to the velocity of the target. Doppler measurements are commonly used to demonstrate velocity variations in blood, walls or vessels of the vascular system, as well as gastric and other moving liquid systems in a patient.

Doppler-shift measurements sometimes entail the use of separate transducers, mounted side by side, for transmitting a continuous wave and for receiving its reflections. Unlike A-scan and B-scan systems, which employ pulses of ultrasound, Doppler systems that rely on a continuous wave of ultrasound cannot provide distance information. (Doppler systems are typically used for measuring blood flow, and range information is not always critical). But there are Doppler systems in which range also plays a part. The transmitter can be gated on so that instead of emitting a long (timewise) continuous wave, only a pulse burst is emitted. By turning the receiver on only at a particular time after the pulse is emitted, the frequency shifts caused only by an object at a fixed location from the source can be ascertained.

More complete descriptions of the use of ultrasound in medicine are to be found in "Ultrasound in Medical Diagnosis", Scientific American, May 1978, pages 98–112, and "The Application of Ultrasound in Medical Diagnosis", Proceeding of the Institution of Radio and Electronics Engineers Australia, November 1978, pages 333–392.

The width of the beam in the area of focus determines the lateral resolution of any system, so that sharp focusing is often desireable. On the other hand, less-focused beams may be desired especially where the region of interest is deep in the examined object and deep penetration is required. (A less-focused beam provides a longer "focal zone", that is, a longer region in the body in which the beam is concentrated, although not as highly concentrated at its narrowest point, in the "focal plane".) The width of an ultrasonic beam may be narrowed by focusing it utilizing lenses or mirrors, employing a curved transducer surface, or using a multi-element transducer whose individual elements are energized at progressively different times to generate the desired beam shape. When performing B-scan measurements, highly focused transducers are usually used in order to provide maximum lateral resolution. This generally entails the use of large-diameter transducers. Doppler measurements, on the other hand, often require a lower degree of focusing. Here, what is desired is the coupling of energy into a region whose depth need not be determined precisely, as long as sufficient energy impinges upon the moving object. Smaller-diameter transducers may or should be used since a less focused beam is actually desired. This is to be contrasted with sharply focused beams obtainable from large-diameter transducers, where maximum lateral resolution is required, but in which the beam diverges widely both in front of and in back of the focal plane.

The distance of the focal plane from the source is dependent upon the diameter of the transducer, its radius of curvature, and the ultrasound frequency. The transducer thickness also controls the frequency of the ultrasound and thus the penetration, since the rate at which ultrasound energy is attenuated is directly proportional to the frequency. Since higher resolution calls for higher-frequency radiation, it is apparent that the higher the resolution, the lower the penetration.

Ultrasound transducers normally operate by resonating in the thickness mode, i.e., the frequency of the transducer is determined solely by its thickness. The transducer diameter and its radius of curvature do not affect frequency; they (along with the frequency) have an effect only on the beam profile, that is, the intensity distribution in space parallel to the transducer face at different distances from the transducer face. With these interrelationships in mind, it will be helpful to consider the relative transducer thicknesses and diameters which are optimum for pulse echo and Doppler measurements.

Doppler operation, pulsed or continuous, advantageously employs a relatively large beam profile to ensure that a blood vessel or other measurement site is completely "enclosed". Thus a relatively small diameter transducer is preferable since it provides a large beam profile along the length of the beam. Because in Doppler operations flow in deep-lying vessels is usually to be measured, a low frequency is preferable. Consider, for example, a beam which must travel from the transducer face through 20 cm of water and then through another 20 cm of a human body to a deep-lying vessel. In burst mode, the maximum pulse rate is approximately 2 kHz as the return time for echoes is about 520 microseconds. With a 2-KHz pulse burst repetition frequency and for flows of 50 cm/sec or higher, the carrier frequency (the frequency at which the transducer oscillates) should be under 2 MHz, as is known in the art.

For pulse echo measurements, on the other hand, for which a sharper focus or narrower beam profile is desired, the transducer should have a larger diameter to obtain high resolution images. But in addition to a larger diameter, the frequency should be higher than that used in Doppler measurements because the higher the frequency, the higher both the axial and lateral resolution. Thus pulse echo measurements, instead of calling for an operating frequency of under 2 MHz, may be most advantageously accomplished at frequencies of 3 MHz or higher.

All things considered, it is apparent that the same transducer is not the best possible for all purposes, and it is for this reason that different transducers are used depending upon the particular type of examination to be conducted. Very often two procedures must be implemented one after the other. For example, suppose Doppler information is desired from a small object, e.g., a fetal heart. A B-scan may first be taken to determine the position of the object, followed by a Doppler scan (with the B-scan positional information being used to gate on the Doppler receiver just at the time when echoes from the object of the interest are received). Especially when the transducer is contained at the end of an arm immersed in a liquid bath, it would be highly advantageous to be able to operate a single transducer element at two different frequencies which can be switched. If it is necessary to physically switch transducer elements, by the time this is accomplished a fetus may have moved, in which case the previously determined positional information is useless.

It is a general object of my invention to provide a system which utilizes a single ultrasound transducer for generating and detecting ultrasound at at least two different frequencies.

It is another object of my invention to provide a system in which a single transducer controls imaging with high resolution at one frequency, and then pulse Doppler measurements at another frequency.

It is a further object of my invention to provide a system in which a single transducer may be used to provide different degrees of focusing in order to obtain different resolution/penetration tradeoffs for normal pulse echo "B scan" imaging.

Briefly, in accordance with the principles of my invention, two transducer elements, of the same or different sizes, thicknesses and/or materials, are bonded together. The transducer is provided with three electrodes, one coating (and bonding to each other) the two facing surfaces, and the other two coating the outer surfaces of the two elements. By using the front electrode, together with one of the other two, different operating frequencies may be employed and different degrees of focusing may be obtained.

At the outset, this arrangement should be distinguished from those of the prior art in which two or more transducer elements were bonded together and provided with a central electrode. Such prior art transducer electrodes were used for the purpose of obtaining either electrical isolation of the central electrode and/or, more commonly, high intensities. Such prior art transducers were not used for varying frequency or degree of focusing.

Further objects, features and advantages of my invention will become apparent upon consideration of the following detailed description in conjunction with the drawing in which:

FIGS. 1A and 1B depict front and side views of the front transducer element utilized in the first illustrative embodiment of the invention;

FIGS. 2A and 2B depict front and side views of the rear transducer element used in the first illustrative embodiment of the invention;

FIG. 3A depicts a front view of the transducer of the first illustrative embodiment of the invention, with the front and rear elements bonded to each other;

FIG. 3B is an enlarged cross-sectional view along the line 3B—3B of FIG. 3A;

Figure 4:
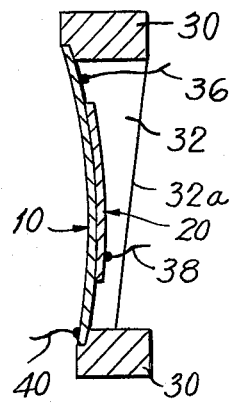
FIG. 4 is a side view illustrating the mounting of the transducer of FIGS. 3A and 3B.

Transducer elements 10 and 20 of FIGS. 1 and 2 are manufactured in a conventional manner by grinding the correct curvatures (which should mate with each other), diameters, and thicknesses from a suitable material such as lead zirconate titanate. In the first illustrative embodiment of the invention, the radius of curvature of each transducer element is 325 mm, and the thickness of each element (depicted by the numerals 10a and 20a) is 0.67 mm. The front transducer element has a diameter of 70 mm, and the rear transducer element has a diameter of 40 mm. (In general, the radius of curvature of the back of the front element should be within 0.01 mm of the radius of curvature of the front of the back element.)

Referring to FIG. 1, the front surface of transducer element 10 is coated with a silver compound 12, and the back surface is coated with a silver compound 14. As is known in the art, the silver coating electrodes may be formed by silk-screening a colloidal silver solution or even by brushing or spraying it on. The electrodes which are thus formed are very thin, e.g., 0.001 inch. Any of the conventional electrode compositions, such as those available from Dupont, may be used. Typically, the transducer element is placed in an oven and held at a temperature between 500° C. and 600° C. in order to have the silver electrodes adhere to the lead zirconate titanate. The transducer element of FIG. 1, by itself, is conventional, and has a resonant operating frequency of 3 MHz. When used by itself, the element of FIG. 1 allows imaging to full depth in the human body, and provides a 20-dB beam width at focus of approximately 5.5 mm. (The term 20-dB beam width is the diameter of the largest circle or contour where the intensity is −20 dB relative to the maximum intensity anywhere in the same plane.)

Front electrode 22 and back electrode 24 of the rear transducer of FIG. 2 are formed in a comparable manner. The main difference between the two transducer elements is their respective diameters. After the two individual elements are formed, additional silver electrode material (approximately the same thickness as the earlier formed electrodes) may be placed on the front of the smaller element and the back of the larger, the additional silver being used to bond the two elements together. The elements are aligned as shown in FIG. 3A and then placed in an oven to bond them together. Although they could be joined by glass or a suitable glue, the use of such materials would probably require first mixing them with a conductive metallic powder such as silver. It is more efficient to bond the two elements to each other by use of electrode material. (No matter how the elements are bonded, and there may be many other ways to accomplish this, there must be an electrical connection, which may be capacitively coupled, and the bond should be ultrasonically transparent.) The composite transducer (see FIG. 3B) includes a front electrode 12, a center electrode 14,22 and a back electrode 20.

When an energizing signal (typically a single pulse) is applied between the front electrode and the center electrode, in effect it is only the front transducer element 10 which need be considered, and its resonant frequency is 3 MHz as described above. But when an energizing signal (typically a burst of 10 pulses at 1.5 MHz) is applied across the front electrode 12 and the back electrode 20 of the composite unit, the resonant frequency is 1.5 MHz since the effective transducer thickness is doubled. In such a case, the 20-dB beam width at focus is approximately 1.6 cm. (The lower frequency results in a longer focal range and less focusing. In general, if the frequency, diameter and curvature of a transducer is known, then its beam width can be calculated, as is known in the art.) Thus conventional B-scans may be performed best by applying the energizing signal across the front and center electrodes, while conventional Doppler measurements may be performed best by applying the energizing signal across the front and back electrodes.

The transducer element of FIG. 3 may be mounted in a conventional manner, as is shown in FIG. 4. Housing 30 is typically cast epoxy, as is known in the art, and the element is attached to the housing by the backing material 32 which is also typically cast epoxy (although the transducers could be clamped and air-backed). As shown by the numeral 32a, the backing material is cut at an angle designed to reduce the detection of any reflections which originate from a sound wave emitted from the back of the transducer. Conventional techniques may then be used to connect wires 36, 38 and 40 to the silver electrodes, by using either silver bearing solder, normal tin/lead solder, a conductive composition glue, or metal-to-metal contact.

Figure 5:
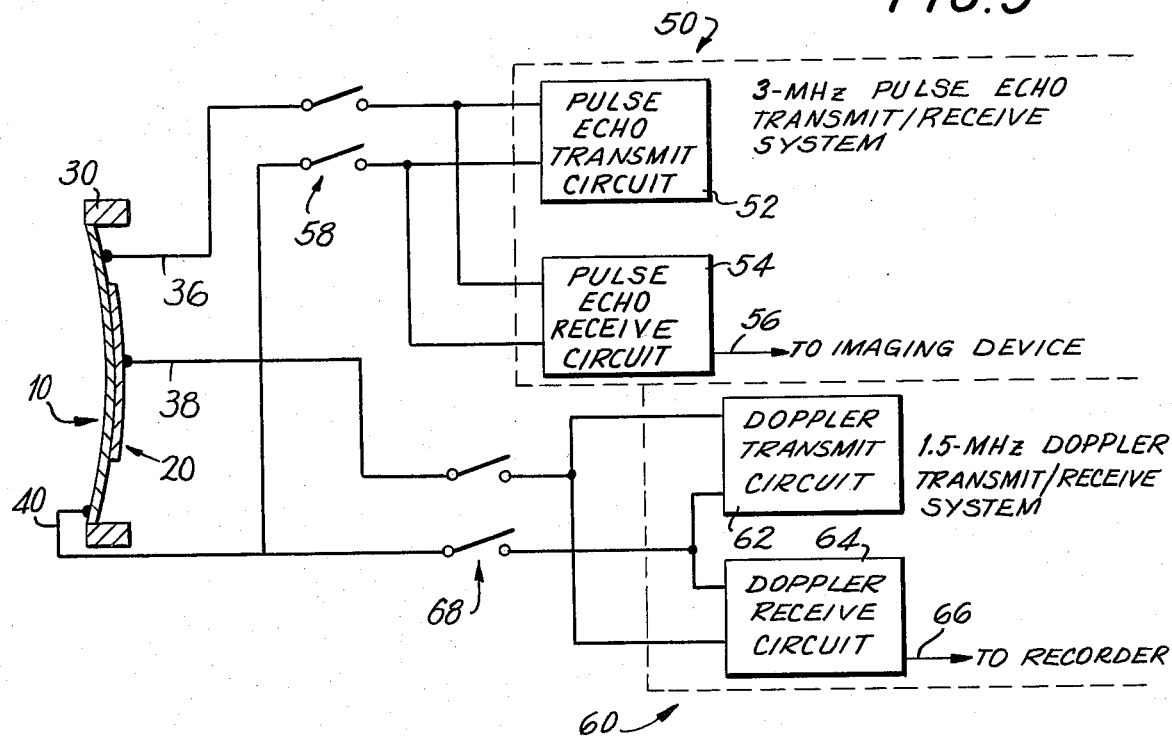
FIG. 5 is a schematic which illustrates use of the transducer of FIGS. 3 and 4 in a first illustrative ultrasound system.

The system of FIG. 5 (a water bath ultrasound system, the bath not being shown) utilizes the transducer of FIGS. 3 and 4 to accomplish B-scan and Doppler measurements. The front and center electrodes may be connected by a switch 58 to a conventional pulse echo transmit circuit 52 and a conventional pulse echo receive circuit 54. These two sub-systems are contained in an overall 3-MHz pulse echo transmit/receive system 50, with the output 56 of the receive circuit being extended to a conventional imaging device. Similarly, switch 68 may be used to connect the front and back electrodes to the Doppler transmit circuit 62 and the Doppler receive circuit 66 of a conventional 1.5-MHz Doppler transmit/receive system 60, with the output 66 of the receive circuit being extended to a conventional recorder. Not shown are the conventional tuning components which may be connected across the transducer, these components typically being resistors and inductors selected to optimize the transducer characteristics as is known in the art. The transducer should be heavily damped and have a broad bandwidth. The Doppler transmit circuit applies a 1.5-MHz signal to the transducer which is resonant at this frequency. In the case of imaging, system 50 applies a single pulse to the transducer which then resonates at 3 MHz. It should also be apparent that electronic switches may be used to allow switching back and forth between the imaging mode of operation and the Doppler mode of operation.

Because the overall transducer thickness is 1.34 mm in the Doppler mode (the operative electrodes are the front and back electrodes of the composite element), the operating frequency in the Doppler mode is 1.5 MHz, as compared with the operating frequency of 3 MHz when the transducer element is used in the pulse echo mode, in which case the operative electrodes are the front and center. Preferably, as in this illustrative embodiment of the invention, the two transducer elements have the same thickness. When operated in the Doppler mode, there is minimum distortion because the center electrode is at a resonant node.

In effect, two separate ultrasound systems utilize the same transducer, the difference being which of the center and back electrodes is used together with the front electrode. The advantage, of course, is that the single transducer can be optimized for two different modes of operation without requiring any change being made to the transducer itself as a change is made in the mode of operation.

Figure 6:
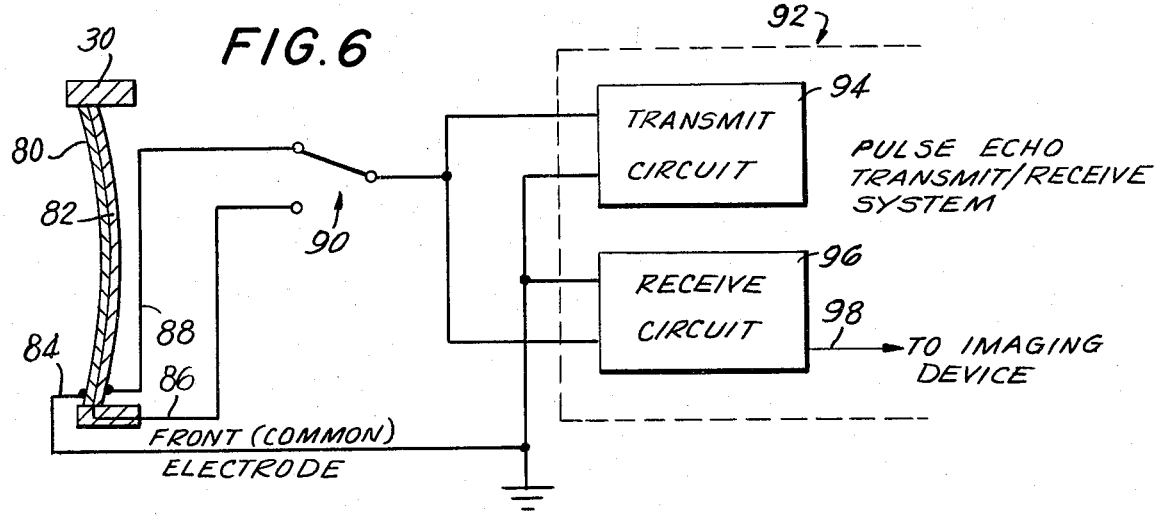
FIG. 6 is a schematic which illustrates use of the transducer of the second illustrative embodiment of the invention in a second illustrative ultrasound system.

In the transducer utilized in the system of FIG. 6 (also a water bath ultrasound system), both transducer elements 80 and 82 have the same 70-mm diameter. More important, while the front element 80 has a thickness of 0.67 mm, the back element 82 has a thickness of 0.50 mm (not drawn to scale). The transducer is used only for pulse echo measurements, but the resonant frequency of the transducer can be selected to be either 3.0 MHz (front element alone) or 1.7 MHz (combined elements). The front electrode is connected by a wire 84 to the ground of both transmit circuit 94 and receive circuit 96, both of which are contained in a conventional pulse echo transmit/receive system 92, with the output of the receive circuit being extended over line 98 to a conventional imaging device. Switch 90 is now used to connect either the center electrode over wire 86 to the transmit and receive circuits, or the back electrode over wire 88 to the transmit and receive circuits. (In the case of the transducer of FIG. 6, the wire 86 connection to the center electrode may be accomplished by cutting a small hole in the rear transducer 82, or by cutting a notch in its edge. Alternatively, the center electrode could wrap around the edge of the rear transducer to a small isolated area on its back to allow a connection to be made.) No matter what the position of the selector switch 90, the transmit circuit 94 delivers a single pulse of energy to the transducer. The transducer then self-resonates at either 1.7 MHz or 3 MHz. Receive circuit 96 is capable of broad band operation in that it must detect returning echoes at either frequency. The 1.7-MHz operation allows greater penetration, but the larger beam width provides less resolution. The 3-MHz operation permits less penetration, but the smaller beam width provides greater resolution in both the lateral and axial directions. For a given transducer diameter and radius of curvature, the transducer will always be more highly focused at a higher frequency than at a lower frequency, but while its resolution will be better the resulting beam penetration will be poorer. The transducers of my invention still offset penetration against degree of focusing, as do the prior art transducers. But the advantage of the transducers of my invention is that without effecting any changes to them, a choice may be made between higher resolution and less penetration, or lower resolution and greater penetration.

Although not shown in FIG. 6, operation at a frequency of 4 MHz would also be possible by energizing just the back element 88. (Operating frequency varies inversely with effective thickness.) Of course, such a 3-frequency system could also be operated in the Doppler mode at one or more of the frequencies.

Although the invention has been described with reference to particular embodiments, it is to be understood that these embodiments are merely illustrative of the application of the principles of my invention. Numerous modifications may be made therein and other arrangements may be devised without departing from the spirit and scope of the invention.

What I claim is:

1. An ultrasonic medical diagnostic system comprising a first transducer element; a second transducer element; electrodes coating the front and back surfaces of both of said transducer elements, with the back electrode of said first transducer element and the front electrode of said second transducer element being bonded together; means for controlling pulse echo operation at one frequency, with relatively low penetration and high resolution, by applying an energizing signal across the front and back electrodes of one of said transducer elements; and means for controlling Doppler operation at another lower frequency, with relatively high penetration and low resolution, by applying an energizing signal across the front electrode of said first transducer element and the back electrode of said second transducer element.

2. An ultrasonic medical diagnostic system in accordance with claim 1 wherein both of said transducer elements are curved and have mating radii of curvature.

3. An ultrasonic medical diagnostic system in accordance with claim 1 wherein said first transducer element has a diameter larger than of said second transducer element.

4. An ultrasonic medical diagnostic system in accordance with claim 1 wherein said first and second transducer elements have the same thickness.

5. An ultrasonic medical diagnostic system in accordance with claim 1 wherein said first and second transducer elements have different thicknesses.

* * * * *